United States Patent [19]
Sternberger et al.

[11] Patent Number: 6,002,960
[45] Date of Patent: Dec. 14, 1999

[54] PASSIVE, NON-INVASIVE METHOD TO QUANTIFY OBJECTIVELY THE LEVEL AND DENSITY OF A NEURAL BLOCKADE

[75] Inventors: Wayne I. Sternberger, Highland; Robert S. Greenberg, Glenelg, both of Md.

[73] Assignee: The Johns Hopkins University, Baltimore, Md.

[21] Appl. No.: 08/918,446

[22] Filed: Aug. 26, 1997

Related U.S. Application Data

[60] Provisional application No. 60/024,663, Aug. 27, 1996.

[51] Int. Cl.$^6$ ........................................................ A61B 5/04
[52] U.S. Cl. ............................................ 600/546; 600/557
[58] Field of Search ..................................... 600/544, 545, 600/546, 555, 557

[56] References Cited

U.S. PATENT DOCUMENTS

| | | | |
|---|---|---|---|
| 5,131,401 | 7/1992 | Westenskow et al. | 600/554 |
| 5,195,531 | 3/1993 | Bennett | 600/546 |
| 5,320,109 | 6/1994 | Chamoun et al. | 600/544 |
| 5,772,591 | 6/1998 | Cram | 600/383 |

*Primary Examiner*—Max Hindenburg
*Assistant Examiner*—Pamela L. Wingood
*Attorney, Agent, or Firm*—Francis A. Cooch

[57] ABSTRACT

Electromyogram, temperature and heart rate measurements, which correlate to the dermatomal level and density of neural blockade, are obtained in a passive manner, i.e., the patient is not stimulated or exposed to any sensor that requires an active conduction in order to make a measurement and no active patient participation or response is required. The measurements obtained provide objective and quantitative indications of, for example, epidural blockade with local anesthetics, thus, allowing objective real-time assessment of density and level of neural blockade.

20 Claims, 3 Drawing Sheets

Typical Monitor Sites

SENSOR ARRAY

Typical Monitor Sites

PASSIVE, NON-INVASIVE METHOD TO QUANTIFY OBJECTIVELY THE LEVEL AND DENSITY OF A NEURAL BLOCKADE

CROSS-REFERENCE TO RELATED APPLICATION

This application claims the benefit of prior filed copending U.S. provisional application Ser. No. 60/024,663, filed Aug. 27, 1996.

BACKGROUND OF THE INVENTION

The invention relates to the monitoring of the effectiveness of anesthetics in humans or animals and, more specifically, provides a method for passively, non-invasively and objectively quantifying the level and density of a neural blockade.

Some qualitative and active response evaluations have been applied to the measurement of neural blockade; however, reliability, repeatability, and inter-patient correlation can be subject to large variation. Confounding difficulties exist when the patient cannot or will not respond to tests such as needle sticks, pinches, or cold stimuli to determine blockade effectiveness. Furthermore, an individual's perception of pain or cold cannot be correlated to a reference standard.

There are limited reports on the effectiveness of using quantitative monitors as a measure of neural blockade while performing comparative studies of anesthetic agents. Studies have recognized the blockade of abdominal muscles using electromyography (EMG) during lumbar epidural analgesia. One such study required active participation from the subject. Others have examined the effect of different local anesthetics on motor blockade and EMG.

Despite the above, it remains the case that there exists no method to quantify, passively and routinely, the anatomic level or density (completeness of block at a particular dermatomal level) of a neural blockade, e.g., local anesthetic epidural blockade, by non-invasive, objective, and automated means.

SUMMARY OF THE INVENTION

The invention solves the above-described problems by monitoring several physiological responses to neural blockade using a set of non-invasive monitors/sensors and related signal processing without active patient participation or response to quantify objectively the blockade's level and density.

The invention is a method for passively, non-invasively, and objectively quantifying the level and density of a neural blockade in a patient, comprising the steps of:

placing a non-invasive sensor for measuring a physiological response to the neural blockade at a site on the patient's body; and monitoring the changes in the physiological response to the neural blockade using the sensor without active participation or response by the patient to quantify the level and density of the neural blockade.

The physiological responses that can be monitored and the methods for monitoring include muscle innervation using surface electromyography (EMG); skin temperature using a temperature sensing means; and heart rate using electrocardiography (EKG).

It has been demonstrated that for muscle innervation the level and density of the neural blockade is quantified by, respectively, the placement of the sensor and a change in the signal amplitude of the surface EMG, wherein the density is inversely proportional to the signal amplitude. For skin temperature, the level and density of the neural blockade is quantified by, respectively, the placement of the sensor and a change in skin temperature, wherein the density of the neural blockade is directly proportional to skin temperature. Finally, for heart rate, the level and density of the neural blockade are quantified by a change in heart rate, wherein the density of the neural blockade is inversely proportional to heart rate.

The method of the invention can be incorporated in an automated system to, for example, control drug delivery to a patient or advise the clinician about patient status including displaying the level and density of the neural blockade from onset to termination. The invention could also be used to monitor neural blockade in animals.

The onset of neural blockade can be objectively monitored by placement of one or more sensors and quantifying a decrease in signal amplitude of a surface EMG; an increase in skin temperature; and changes in heart rate. Moreover, the blockade density determined by these objective means appears to compare favorably with the results of traditional subjective methods. Thus, the invention provides the anesthesiologist with positive information regarding the level and density of neural blockade in a non-invasive manner without requiring active patient participation or response.

DETAILED DESCRIPTION OF THE INVENTION

The method of the invention uses non-invasive sensors placed at one or more sites on a patient's body to monitor primary and reference parameters, as follows:

Primary

Muscle Innervation—spontaneous surface EMG

Temperature—Peripheral—skin-mounted thermocouple

Heart Rate (HR) and HR Variability—Lead-II electrocardiogram (EKG)

Reference

Ambient Temperature—in-air thermocouple

Core Body Temperature—tympanic thermocouple

Figure 1A:
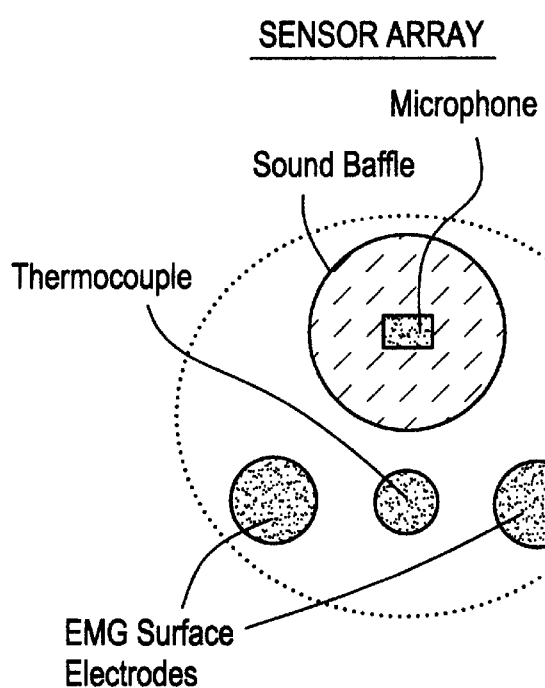
FIG. 1, consisting of FIGS. 1a and 1b, illustrates, respectively, an example of a sensor array for collection of data for use in the method of the invention, and representative sites on the human body for placement of such sensor arrays and of other data collection devices.
Figure 1B:
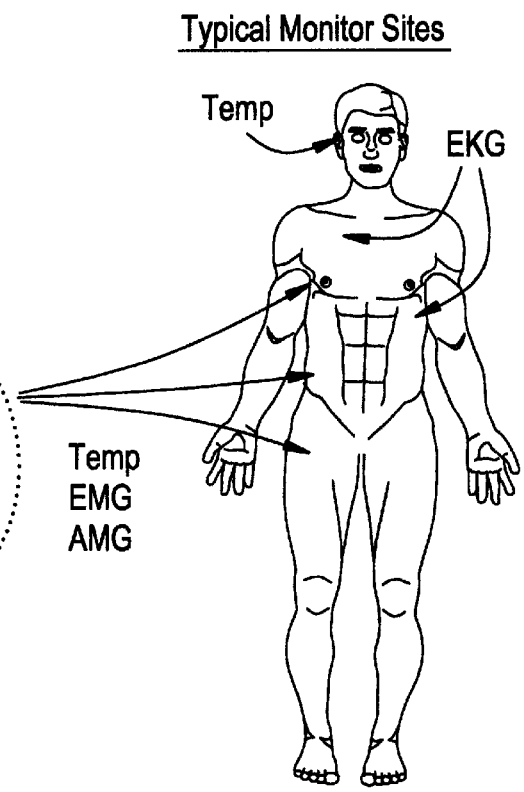

A non-invasive sensor array that includes sensors for EMG, AMG (in the below-described study), and peripheral temperature (FIG. 1a) is placed at each monitor site; EKG and reference sensors are applied where and/or as appropriate (FIG. 1b). Splash-proof coverings can be used to protect each monitor site.

To discriminate the cephalo-caudal spatial effect of the neural block it is preferable to use multiple monitor sites as shown in FIG. 1. In the clinical tests described below, three specific sites were identified for use: the fourth thoracic dermatome (nipple, T4) and tenth thoracic dermatome (umbilicus, T10) levels on the anterior axillary line and the anterior of the thigh, representing the second lumbar dermatome (L2).

For muscle innervation the level and density of the neural blockade is quantified by, respectively, the placement of the sensor array and a change in the signal amplitude of the surface EMG, wherein the density is inversely proportional to the signal amplitude. For skin temperature, the level and density of the neural blockade is quantified by, respectively, the placement of the sensor array and a change in skin temperature, wherein the density of the neural blockade is directly proportional to skin temperature. Finally, for heart rate, the level and density of the neural blockade are quantified by a change in heart rate, wherein the density of the neural blockade is inversely proportional to heart rate.

The invention was demonstrated in a study involving seven men (Table 1) who were all undergoing elective radical retropubic prostatectomy using lumbar epidural blockade.

TABLE 1

Subject Demographics

| Subject | Age (Years) | Weight (kg) | ASA Status | Epidural Site | Time-to-Incision (min) | Notes |
|---|---|---|---|---|---|---|
| 1 | 55 | 85.7 | 2 | L4–5 | N/A | Combined GA and Regional due to history of apnea; epidural dosed after incision |
| 2 | 42 | 83 | 2 | L4–5 | 17.0 | |
| 3 | 47 | 78 | 2 | L2–3 | 17.7 | |
| 4 | 63 | 104 | 2 | L2–3 | 12.5 | |
| 5 | 55 | 103 | 2 | L3–4 | 15.0 | |
| 6 | 65 | 110 | 2 | L3–4 | 29.3 | Converted to combined GA and Regional |
| 7 | 60 | 88 | 2 | L–5 | 15.5 | |

Time from main epidural dose to start of incision

Spontaneous surface electromyogram (EMG), acoustomyogram (AMG) and temperature (T) measurements were made along the anterior axillary line at T4, T10, and L2 dermatomal levels along with Lead-II electrocardiogram (EKG). Reference measurements included tympanic and ambient temperature, and ambient sound. As discussed below, time-series data were acquired before epidural dosing and at predefined intervals after dosing. A dedicated PC-based system provided system control and data storage.

Based on the predicted temporal response to epidural dosing, data epochs were collected immediately prior to the main epidural dose (baseline) and at 2, 5, 10, 15, 20, 25, 30, 45, 60, 75, and 90 minutes after dosing. The epochs were designed to have a minimum duration of 20 seconds. Temperature data records were time-continuous, starting immediately after the thermocouples were placed and ending approximately 2 minutes after the last EMG/AMG/EKG sampling epoch.

Table 2 below summarizes the data acquisition conditions for the parameters of interest.

TABLE 2

Data Acquisition Conditions for Monitored Parameters

| Parameter | Passband (HZ) | Sampling Rate (sec$^{-1}$) | No. of Channels |
|---|---|---|---|
| AMG | 0.5–100 | 1000 | 4 |
| EKG | 2–100 | 1000 | 1 |
| EMG | 10–500 | 2000 | 3 |
| Temperature | DC–0.02 | 0.2 | 6 |

As discussed below, root-mean-square (rms) of EMG and AMG, average T, and average heart rate (R-R interval) were assessed for the levels as a function of time relative to epidural dosing. Changes in objectively monitored variables were compared to qualitative assessment (e.g., pinch test) of the block effectiveness.

Both EMG and AMG are broadband signals that contain information in the time and frequency domains. What is needed is a single derived value that is descriptive of the instantaneous physiological condition of the patient. Typically, the power in the signal provides such an indication in the time domain. Power is proportional to the square of the amplitude of the signal. And, for a signal that has a non-constant (e.g., alternating current) component, it is necessary to average over a finite period of the signal in order to generate a meaningful value. EMG assessments have traditionally computed the average rectified EMG (AREMG) or the rectified integrated EMG (RIEMG), given by:

$$AREMG = RIEMG = \left(\sum_{i=1}^{n} |x_i|\right) \bigg/ n$$

The historical computation methods are clearly not power indicators, so the invention uses the root-mean-square (rms) estimator:

$$rms = \sqrt{\sum_{i=1}^{n} x_i^2 / n}$$

(Note, other methods, e.g., spectral analysis, bi-spectral analysis, etc., may also be useful. The gradient of the signals may also provide useful information.)

Regardless of the method used, selection of the integration interval (i.e., the value of n) is an important factor. The value of n is inversely proportional to the upper frequency response characterized by the computation. An integration interval was selected that retained as much of the passband information as is practical. EMG are integrated over 50 msec (n=100) and AMG signals are integrated over 250 msec (n=250).

Many discrete rms computations are possible within 20-second sampling epochs. Running rms values are computed. The rms value at t=0 includes the first n data points in a series. Subsequent rms values incrementally delete the earliest data point and add the next latest point of the series. The minimum value of the computed rms sequence is selected as representative of the muscle-only condition for any pre-defined sampling epoch.

The time-series data from the study subjects demonstrated that EMG and AMG signals contained noise artifacts that correlated to the use of the electrocautery, suction, and other electronic systems. The slope and intercept of the frequency spectra of the data were used as acceptance criteria to validate that the rms data values were devoid of noise.

The absolute value of EMG signals can be influenced by conditions such as skin conductance, skin temperature, electrode displacement, and site preparation. To mitigate discrepancies, the EMG data were normalized, which involved applying a gain factor that resulted in an expansion or compression of the histogram of the raw data sets. Based on a common time epoch for all study subjects, EMG data were normalized such that the basis histogram contained 50% of all data values between ±5 mV. Other epochs were scaled by the same gain factor calculated for the basis.

It was apparent that AMG signal artifacts were correlated to motions directly induced by the surgeons or indirectly induced by movements near the patient. AMG data are compensated, on a sample-by-sample basis, for the presence of acoustically transmitted noise by subtraction of the ambient signal level.

Changes in skin temperature are adversely influenced by changes in both body core temperature and ambient air temperature. To accommodate these conditions, the raw $(t_{DL,SI})$ dermatome temperature value is standardized $(T_{DL,SI})$ by the tympanic and ambient temperatures as in the following:

$$T_{DL,SI} = t_{DL,SI} - [t_{Tympanic,SI} - t_{Tympanic,0}] - [t_{Ambient,SI} - t_{Ambient,0}]$$

where DL is the dermatome level and SI is the sampling interval. SI=0 correlates to the data epoch before the main epidural dose. Standardized temperature data were then parsed into 20-second segments that correlated with the EMG/AMG/EKG sampling epochs. The average of each of the normalized epochs was computed as a simple arithmetic mean of the data.

Each study subject's average heart rate was determined from the lead-II EKG data sets. The average for the 20-second data intervals was computed as a simple arithmetic mean of the related R-to-R intervals. The occurrence of the leading edge of the R peak was determined by an automated algorithm.

The data revealed three notable aspects of the EMG signals. First, EMG signal amplitude decreased at a rate inversely related to the number of dermatomal levels separating the monitor site and the epidural catheter. That is, the signals at the more cephalad dermatomal levels decreased later than the more caudal levels. Second, after a period of time (between 15 and 30 minutes), all EMG signal amplitudes assumed a generally constant and lower level than at initiation of the primary dose. Third, the constant level at the L2 dermatomal level was approximately 30% lower than that of the T4 and T10 dermatomal levels, perhaps indicating that effective block was created at this discrete level simply by the test dose.

Average temperature trends for the tympanic- and ambient-compensated data all showed a gradual increase as a function of time; longer onset was noted at more rostral dermatomal levels. Heart rate increased by an average of 7.8±9.2 bpm to 10 minutes following initiation of the primary dose, then decreased an average of 19.0±10.8 bpm in the following 15 minutes.

In sum, temporal changes in EMG, skin surface temperature, and heart rate were associated with adequate blockade and correlated to the clinical assessment of the level and density of the block. During block onset the rms EMG signal level decreased >15 mV, temperature increased >1° C., and EKG decreased >7 beats per minute (bpm). AMG showed primary correlation to external influences; response to the block was not evident in the presence of noise.

Figure 2:
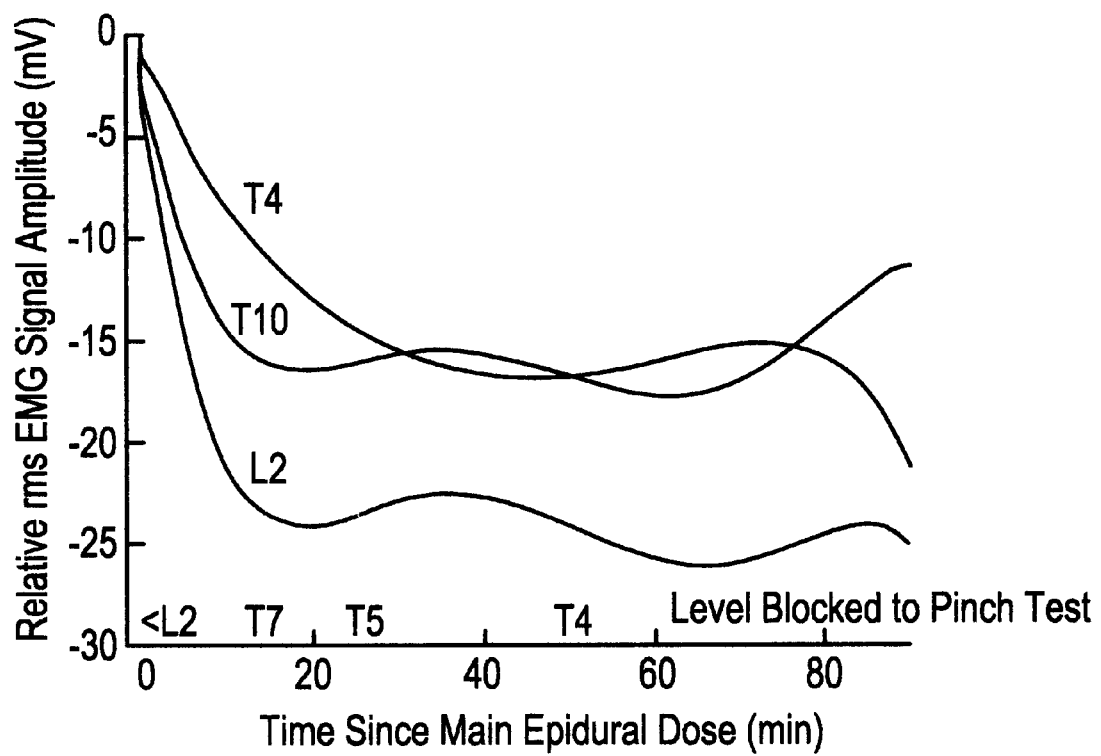
FIG. 2 shows a set of curves of the rms EMG signal amplitudes taken from seven patients who consented to be subjects in a study of the method of the invention.

FIG. 2 shows a set of curves of the rms EMG signal amplitudes for all seven subjects. The data are fifth-order polynomial curves fit to the normalized signal amplitudes for the seven study subjects at each of three monitor levels. The plot also indicates the typical dermatomal level of blockage achieved, according to pinch tests administered by the attending anesthesiologist. Time is referenced to the administration of the main epidural dose (t=0) and the baseline data set is plotted at t=−1 minute. The traces are normalized to the baseline by subtracting the respective baseline value from each successive data point. The time between the main dose and the surgical incision was 17±6 minutes. Lower amplitude limits of the L2 and T10 signals are reached sooner (t=15 minutes) than the T4 signal (t=30 minutes). This suggests that the L2 and T10 levels achieve onset before the T4 level, as expected.

Figure 3:
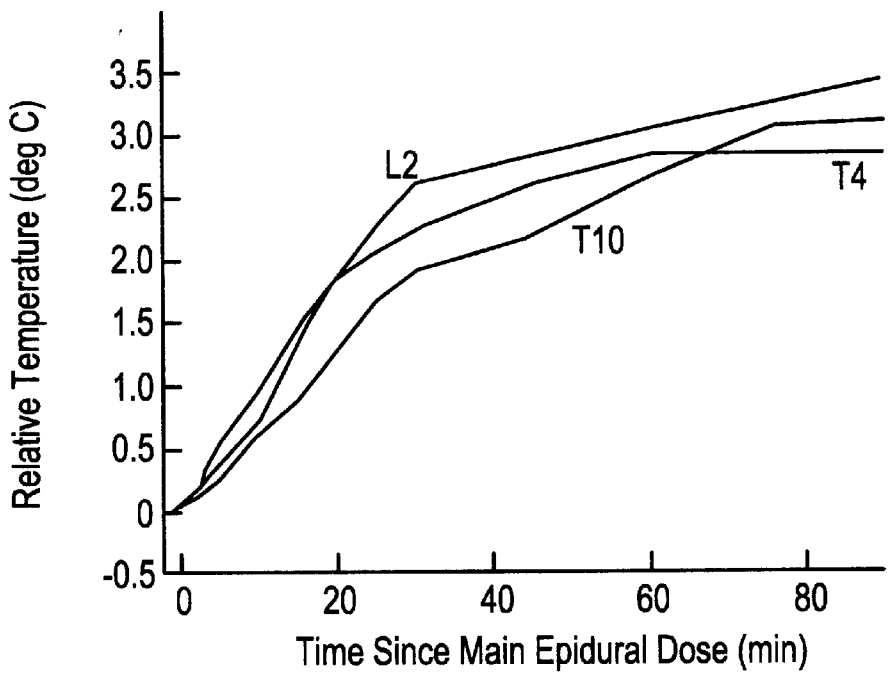
FIG. 3 shows average temperature data for the dermatomal levels for all seven study subjects.

FIG. 3 presents average temperature data for the dermatomal levels for all seven subjects. All levels exhibit the same upward trend as a function of time; they approach a relative increase of approximately 3.5° C. over the 90-minute data collection period. The changes in temperature reflect the effect of sympathectomy upon administration of local anesthetic. These changes also suggest differences in the contribution of blood volume changes and vascular relaxation at each dermatomal level.

Figure 4:
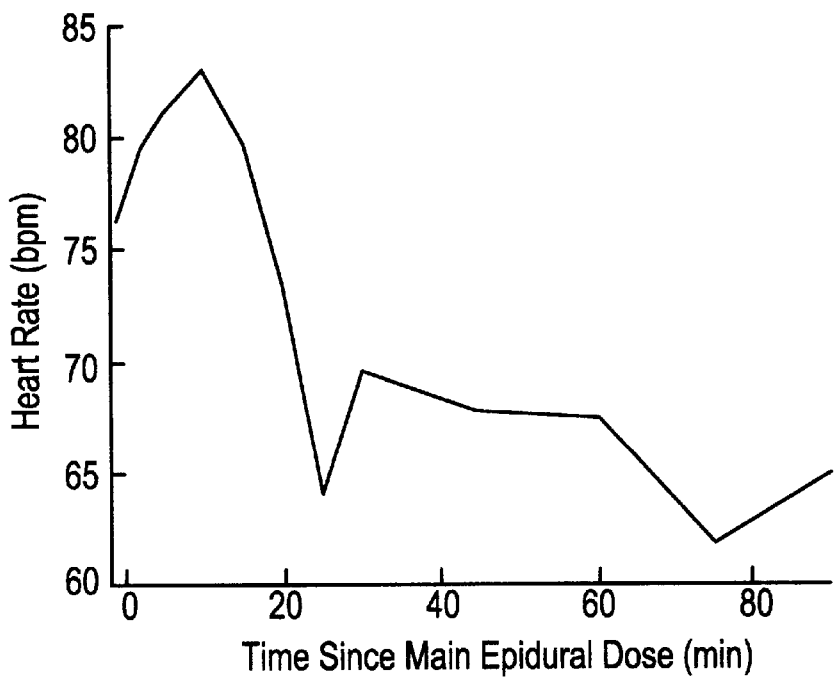
FIG. 4 shows the average heart rate for all seven study subjects.

The average heart rate for all seven subjects is shown in FIG. 4. These data conform to the previously reported effect of local anesthetic on the cardiac accelerator fibers in the T1–T4 spinal segments.

The use of passive and non-invasive monitors to objectively distinguish the level and density of neural blockade as a function of time, and as related to the administration of local anesthetic, has been examined. The data from the EMG, temperature, and EKG monitors, combined with the clinical assessment provided by the anesthesiologist and the conditions of the operative procedure, confirm that an objective measure of block level and density can be performed in the clinical setting.

A universal neural blockade monitor must be fully functional regardless of when it is applied, relative to the administration of the anesthetic agent. The rate of change, or gradient, of the absolute signals presents salient information. The most compelling indicator is the change in EMG signal level between the time of zero minutes and 10 minutes, as shown in FIG. 2. Level L2 decreases approximately 1.5 times that of T10 and 2.5 times that of T4.

Using the monitored parameters in combination rather than singly will enhance the utility of a universal monitor. The weighted summation of EMG and temperature will likely satisfy the basic requirement for a level-discriminating determination of block density.

The method of the invention can be integrated into an automated system for controlling drug delivery to the patient or simply notifying the physician or nurse about patient status, e.g., during post-op recovery. The invention is also applicable to use with animal patients.

The onset of neural blockade can be objectively monitored by placement of one or more sensors and quantifying a decrease in signal amplitude of a surface EMG; an increase in skin temperature; and changes in heart rate. Moreover, the blockade density determined by these objective means appears to compare favorably with the traditional subjective method of pinch-tests. The invention provides the anesthesiologist with a passive, objective tool for real-time, non-invasive monitoring of the level and density of neural blockade.

We claim:

1. A method for passively, non-invasively and objectively quantifying the level and density of a neural blockade in a patient, the method comprising the steps of:

placing a non-invasive sensor for measuring a physiological response to the neural blockade at a site on the patient's body; and monitoring the changes in the physiological response to the neural blockade using the sensor without active participation or response by the patient to quantify the level and density of the neural blockade.

2. The method as recited in claim 1, the physiological response comprising muscle innervation.

3. The method as recited in claim 2, the monitoring step comprising the step of monitoring muscle innervation using surface electromyography (EMG).

4. The method as recited in claim 3, wherein the level and density of the neural blockade is quantified by, respectively, the placement of the sensor and a change in the signal amplitude of the surface EMG.

5. The method as recited in claim 4, wherein the density of the neural blockade is inversely proportional to the signal amplitude of the surface EMG.

6. The method as recited in claim 4, wherein the level and density of the neural blockade is quantified by, respectively, the placement of the sensor and a change in the root-mean-square (rms) EMG signal power.

7. The method as recited in claim 6, wherein the density of the neural blockade is inversely proportional to the rms EMG signal power.

8. The method as recited in claim 5, the physiological response further comprising skin temperature.

9. The method as recited in claim 8, the monitoring step further comprising the step of monitoring skin temperature using a means for sensing temperature.

10. The method as recited in claim 9, wherein the level and density of the neural blockade is quantified by, respectively, the placement of the sensor and a change in skin temperature.

11. The method as recited in claim 10, wherein the density of the neural blockade is directly proportional to skin temperature.

12. The method as recited in claim 11, wherein the skin temperature is standardized by the tympanic and ambient temperatures.

13. The method as recited in claims 5 or 11, the monitoring step further comprising the step of monitoring heart rate using electrocardiography (EKG).

14. The method as recited in claim 13, wherein the level and density of the neural blockade is quantified by a change in heart rate.

15. The method as recited in claim 14, wherein the density of the neural blockade is inversely proportional to heart rate.

16. The method as recited in claim 15, wherein the heart rate is averaged over the R—R intervals.

17. The method as recited in claim 15, further comprising the step of automatically controlling the delivery of an anesthetic to the patient using the quantified level and density of the neural blockade.

18. The method as recited in claim 15, further comprising the step of displaying the level and density of the neural blockade.

19. The method as recited in claim 18, further comprising the step of providing automatic notification of the level and density of the neural blockade.

20. The method as recited in claim 15, wherein the neural blockade is a local anesthetic epidural blockade.

* * * * *